(12) United States Patent
Diamond et al.

(10) Patent No.: US 8,948,849 B2
(45) Date of Patent: Feb. 3, 2015

(54) SYSTEM AND METHOD FOR OPTODE AND ELECTRODE POSITIONING CAP FOR ELECTROENCEPHALOGRAPHY, DIFFUSE OPTICAL IMAGING, AND FUNCTIONAL NEUROIMAGING

(71) Applicant: The Trustees of Dartmouth College, Hanover, NH (US)

(72) Inventors: Solomon G. Diamond, Hanover, NH (US); Paolo Giacometti, Wilder, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/863,183

(22) Filed: Apr. 15, 2013

(65) Prior Publication Data

US 2013/0303874 A1    Nov. 14, 2013

Related U.S. Application Data

(63) Continuation of application No. PCT/US2011/056566, filed on Oct. 17, 2011, and a (Continued)

(51) Int. Cl.
| | | |
|---|---|---|
| *A61B 6/00* | (2006.01) | |
| *A61B 5/0478* | (2006.01) | |
| *A61B 5/00* | (2006.01) | |
| *A61B 5/1455* | (2006.01) | |

(52) U.S. Cl.
CPC .............. *A61B 5/0478* (2013.01); *A61B 5/0077* (2013.01); *A61B 5/14553* (2013.01)
USPC .......................................... 600/473; 600/476

(58) Field of Classification Search
CPC . A61B 5/0478; A61B 5/0077; A61B 5/14553
USPC .................................................. 600/473–480
See application file for complete search history.

(56) References Cited

U.S. PATENT DOCUMENTS

| 5,321,501 A | 6/1994 | Swanson et al. |
| 5,361,316 A | 11/1994 | Tanaka et al. |

(Continued)

FOREIGN PATENT DOCUMENTS

| DE | 9308617 U1 | 7/1993 |
| WO | 2007048039 A1 | 4/2007 |
| WO | 2009134674 A1 | 11/2009 |

OTHER PUBLICATIONS

International Search Report and Written Opinion issued in PCT/US2011/056566 dated May 29, 2012, 11 pages.

(Continued)

*Primary Examiner* — Sanjay Cattungal
(74) *Attorney, Agent, or Firm* — Lathrop & Gage LLP

(57) ABSTRACT

An electroencephalographic electrode and optode positioning device has the form of a cap suitable for placement on a subject's head. The cap has semirigid telescopic structures that stiffen it to provide accurate electrode and optode spacing, and stability during subject activity. The cap is intended for use in functional neuroimaging and, although its materials are compatible with fMRI, is usable without fMRI to permit study of physically as well as mentally active subjects.

16 Claims, 21 Drawing Sheets

Related U.S. Application Data continuation-in-part of application No. 12/990,159, filed as application No. PCT/US2009/041560 on Apr. 23, 2009, now Pat. No. 8,527,035.

(60) Provisional application No. 61/393,837, filed on Oct. 15, 2010, provisional application No. 61/048,446, filed on Apr. 28, 2008.

(56) References Cited

U.S. PATENT DOCUMENTS

| | | | |
|---|---|---|---|
| 5,842,995 | A | 12/1998 | Mahadevan-Jansen et al. |
| 6,445,939 | B1 | 9/2002 | Swanson et al. |
| 6,485,413 | B1 | 11/2002 | Boppart et al. |
| 7,091,500 | B2 | 8/2006 | Schnitzer |
| 7,295,311 | B2 | 11/2007 | Nicoli et al. |
| 7,428,052 | B2 | 9/2008 | Fujita |
| 7,533,681 | B2 * | 5/2009 | Miller .......... 135/130 |
| 8,214,010 | B2 | 7/2012 | Courtney et al. |
| 2004/0106856 | A1 * | 6/2004 | Kimura .......... 600/310 |
| 2004/0260148 | A1 | 12/2004 | Schnitzer |
| 2005/0143664 | A1 | 6/2005 | Chen et al. |
| 2005/0251116 | A1 | 11/2005 | Steinke et al. |
| 2006/0146338 | A1 | 7/2006 | Fujita |
| 2007/0188855 | A1 | 8/2007 | Shishkov et al. |
| 2008/0177138 | A1 | 7/2008 | Courtney et al. |
| 2008/0177139 | A1 | 7/2008 | Courtney et al. |
| 2008/0177183 | A1 | 7/2008 | Courtney et al. |
| 2009/0018393 | A1 | 1/2009 | Dick et al. |
| 2009/0043191 | A1 | 2/2009 | Castella et al. |
| 2009/0054791 | A1 | 2/2009 | Flusberg et al. |
| 2009/0088619 | A1 * | 4/2009 | Turner et al. .......... 600/383 |
| 2009/0182209 | A1 | 7/2009 | Benni |
| 2010/0069721 | A1 | 3/2010 | Webler et al. |
| 2011/0137124 | A1 | 6/2011 | Milner et al. |

OTHER PUBLICATIONS

U.S. Appl. No. 12/990,159 select file history dated Jun. 11, 2012 through Jun. 5, 2013, 52 pages.

Hamamatsu Photonics K.K., "Multi-Fiber Adapter (MFA) for NIRO-200" brochure, Japan, 3 pages, 2005.

Hamamatsu Photonics K.K., "NIRO-200 Near Infrared Oxgenation Monitor" brochure, Japan, 2 pages, 2003.

Schwarz, et al., "Ball Lens Coupled Fiber-Optic Probe for Depth-Resolved Spectroscopy of Epithelia Tissue," Optics Letters, vol. 30, No. 10, pp. 1159-1161, May 15, 2005.

Robinson, "GRIN Lenses Used in Microendoscope," Biophotonics International, pp. 60-61, Jul. 2004.

International Search Report and Written Opinion issued in related PCT Patent Application Serial No. PCT/US2009/041560, 19 pages, dated Oct. 21, 2009.

Invitation to Pay Fees issued in related PCT Patent Application Serial No. PCT/US2009/041560, 8 pages, dated Apr. 23, 2009.

International Search Report and Written Opinion issued in related PCT Patent Application Serial No. PCT/US2011/056566, 11 pages, dated May 29, 2012.

* cited by examiner

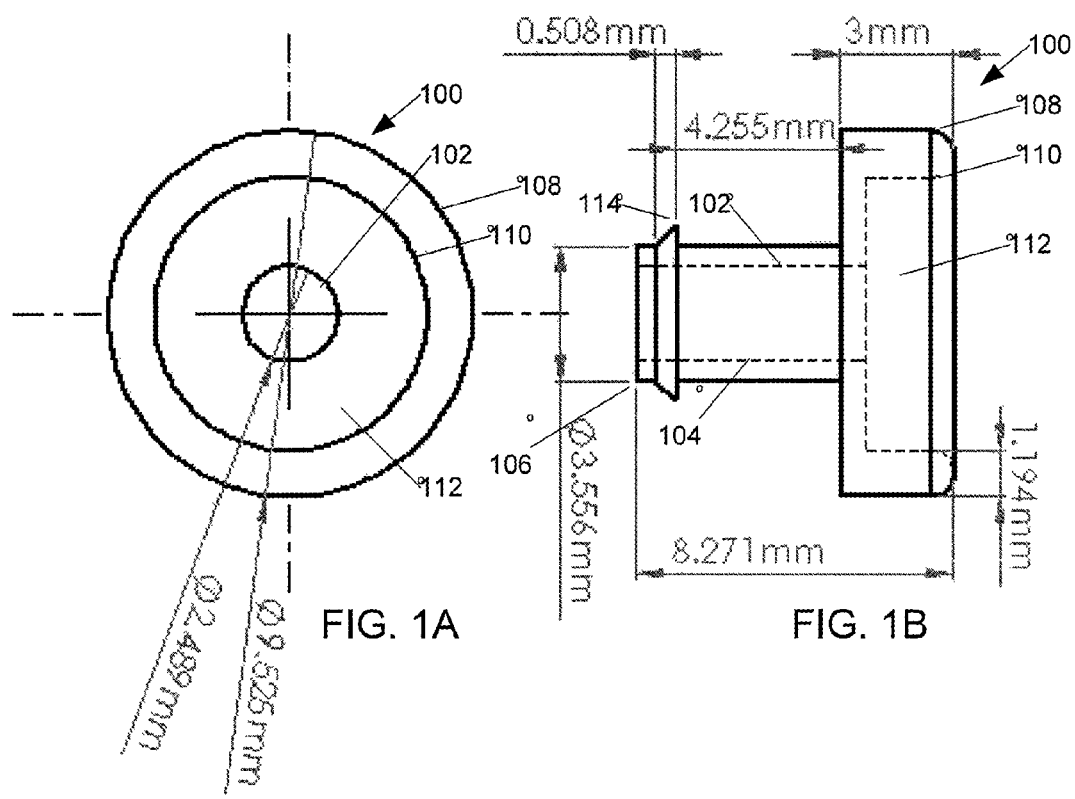

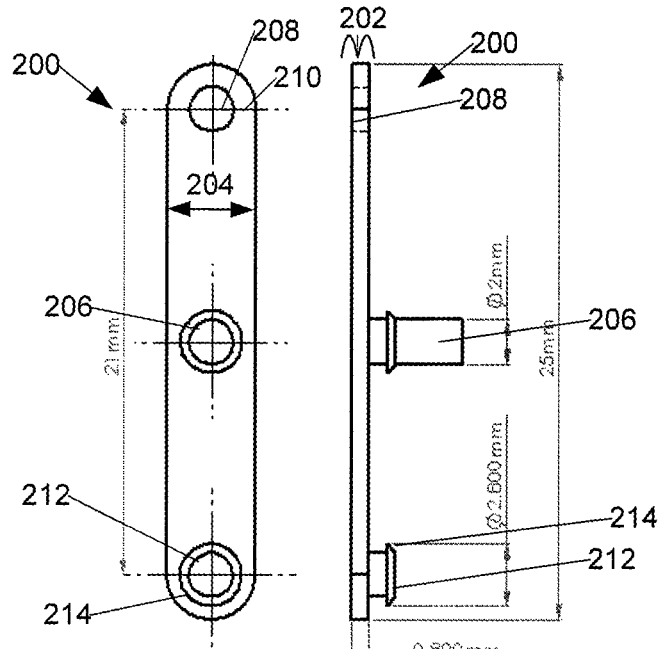
FIG. 3A
FIG. 3B
FIG. 3C
FIG. 3D
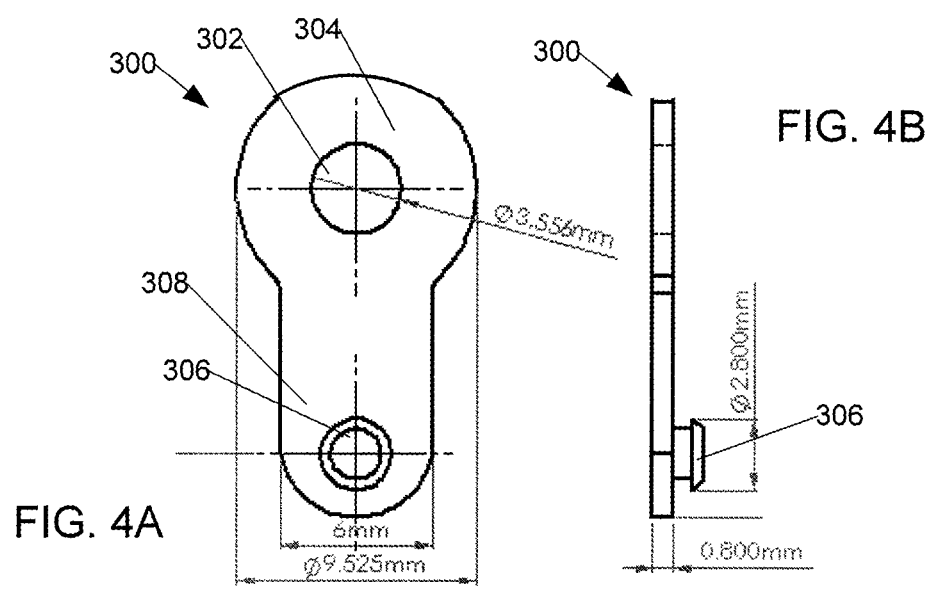
FIG. 4A
FIG. 4B

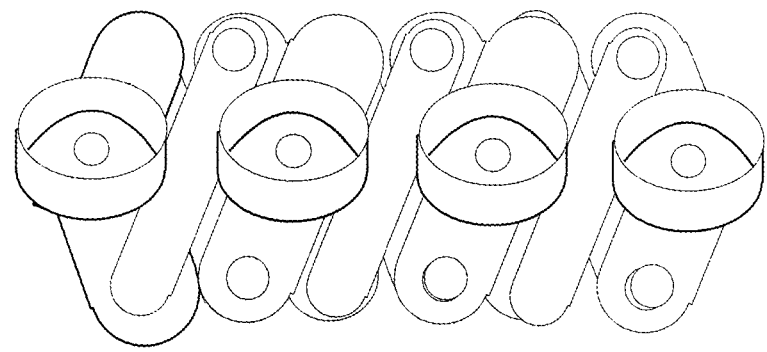
Fig 7
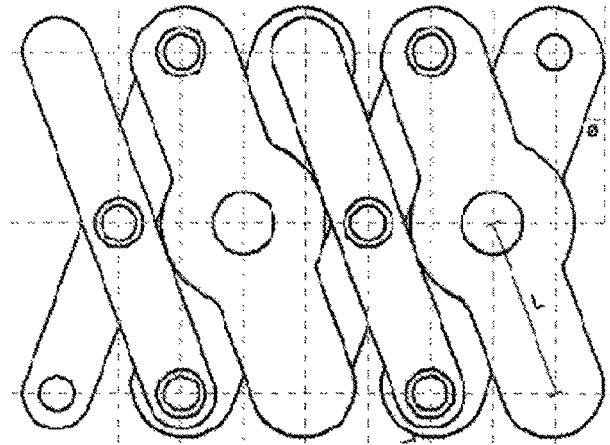
Fig 8
Fig 8A
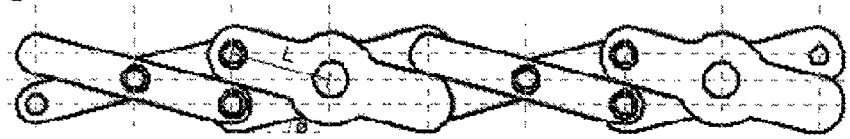

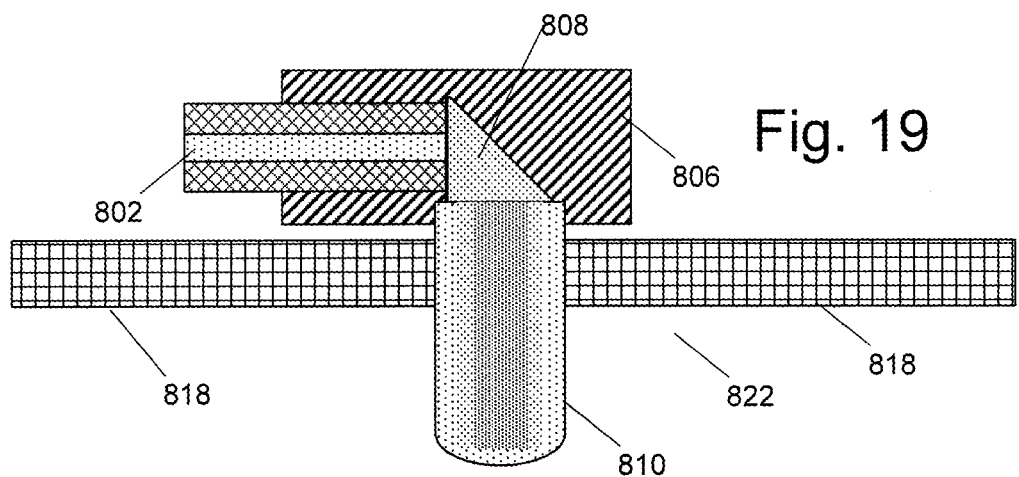
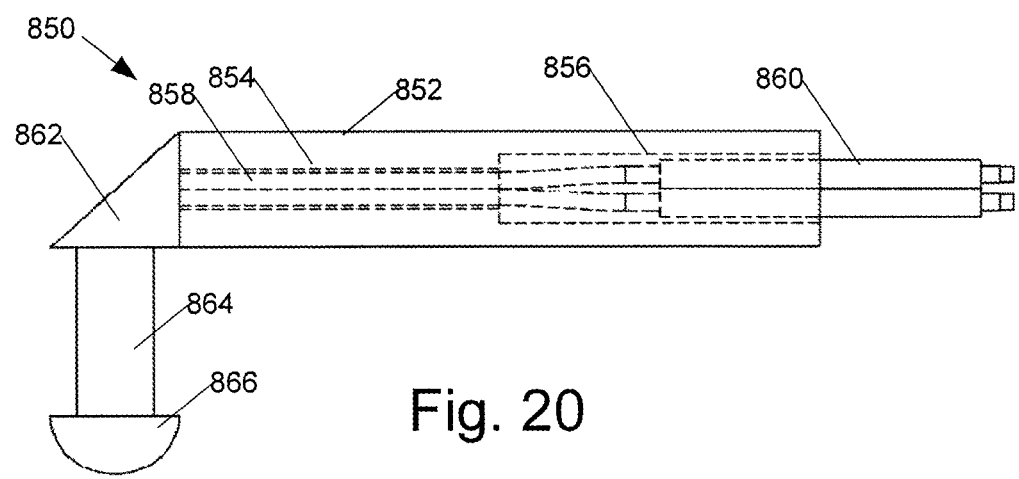
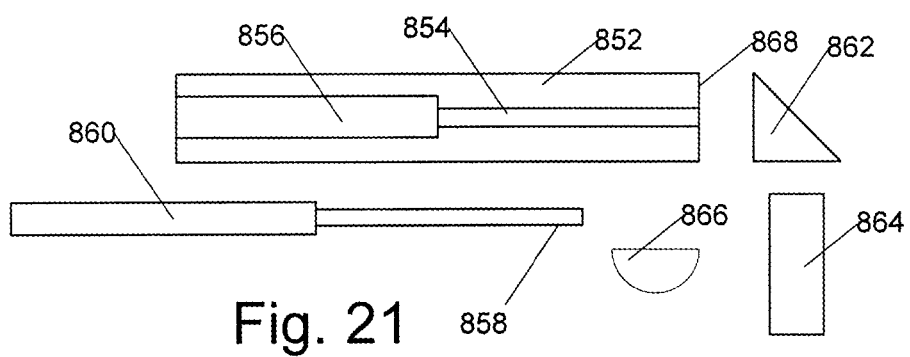

SYSTEM AND METHOD FOR OPTODE AND ELECTRODE POSITIONING CAP FOR ELECTROENCEPHALOGRAPHY, DIFFUSE OPTICAL IMAGING, AND FUNCTIONAL NEUROIMAGING

RELATED APPLICATIONS

This application is a continuation of PCT Patent Application PCT/US2011/056566 which claims right of priority to U.S. Provisional Patent Application 61/393,837 filed 15 Oct. 2010. The present document also claims priority to U.S. patent application Ser. No. 12/990,159 filed 28 Oct. 2010, which in turn claims priority to PCT/US2009/041560 filed 23 Apr. 2009, which in turn claims priority to U.S. provisional patent application No. 61/048,446, filed Apr. 28, 2008.

FEDERAL RIGHTS

The work described herein has been supported by the United States Department of Education grant number P116Z080112 and the United States National Institutes of Health—National Institutes of Aging grant number R21AG033256. As such the United States Government may have certain rights to the inventions described herein.

FIELD

The present document pertains to the fields of electroencephalography, diffuse optical imaging, and functional neuroimaging.

BACKGROUND

When performing electroencephalograms, in order to ensure repeatability and allow comparison of patient data to norms, it is desirable to place EEG scalp electrodes according to the internationally standardized "10-20" pattern; the pattern allows for up to sixty-five electrodes for receiving signals from both cerebral hemispheres.

Some technicians measure electrode placements according to the 10-20 pattern, and attach electrodes individually with a collodion adhesive. Each electrode typically also has a contact surface moistened with an electrically conductive paste. While effective, this technique is very time consuming, especially where many electrodes are required; this technique is failure prone in that individual electrodes may fall off or need adjustment to perform correctly.

A prior technique for positioning scalp electrodes is to fabricate an elastomeric cap and attach electrodes to the cap. Typically, each electrode is on an interior surface of the cap and connects through a hole to a lead exterior to the cap. The leads are then gathered into a cable and connected to an electroencephalograph. The electroencephalograph can provide information regarding electrical activity in the brain.

An optode is a device for transmitting or receiving light into or through tissue. An optode is a device for coupling light between an optical fiber and tissue, such as skin, as described in our previous patent applications 61/048,446 filed Apr. 28, 2008, and PCT/US09/41560 filed Apr. 23, 2009, the disclosure of which is incorporated herein by reference.

Recent research has demonstrated that useful information can be obtained by passing infrared light into the skull from one or more transmit optodes, and receiving that light at one or more receive optodes. In some systems, individual optodes may serve alternately as transmit and receive optodes. Typically, the light is at two or more wavelengths, and information regarding patterns of brain oxygenation is obtained by measuring differences in attenuation at the two or more wavelengths along paths between optodes. Brain oxygenation patterns have been shown to correlate with patterns of neurological activity in the brain; these patterns are therefore useful for functional neuroimaging.

In order to obtain repeatable, useful, indications of patterns of brain oxygenation, it is desirable that optodes be held in a preferred orientation and contact with the scalp. Further, if simultaneous electroencephalography is desired, it is desirable that electrodes also be held firmly in evenly spaced positions conforming to a 10/20 pattern or to an extrapolated 10/20 pattern. It has been found that a simple elastomeric cap fails to hold optodes and electrodes in proper positions and orientations relative to a subject's head and scalp for optimum results, particularly when the subject is physically active.

SUMMARY

An electroencephalographic electrode and optode positioning device has the form of a cap suitable for placement on a subject's head. The cap has semirigid telescopic structures that stiffen it to provide accurate electrode and optode spacing, and stability during subject activity. The cap is intended for use in functional neuroimaging and, although its materials are compatible with fMRI, is usable without fMRI to permit study of physically as well as mentally active subjects.

BRIEF DESCRIPTION OF THE FIGURES

FIG. 1A is a bottom view of an electrode.
FIG. 1B is a side view of the electrode of FIG. 1A.
FIG. 3A is a top view of a narrow link having a central stud.
FIG. 3B is a side view of the narrow link of FIG. 3A.
FIG. 3C is a top view of a narrow link having a central hole instead of a central stud, but otherwise resembling the narrow link of FIG. 3A.
FIG. 3D is a side view of the narrow link of FIG. 3C.
FIG. 4A is a top view of a single-ended semirigid link having an end hole for pivoting on the electrode of FIG. 1A and an end stud.
FIG. 4B illustrates a side view of the single-ended semirigid link of FIG. 4A.
FIG. 7 is a perspective view of a bottom of a 4-electrode subassembly of FIG. 6.
FIG. 8 illustrates subassemblies in retracted position.
FIG. 8A illustrates subassemblies in extended position.

FIG. 19 is a cross section illustration of the embodiment of an optode of FIG. 17, with the optode assembled and inserted into an optode-electrode positioning cap.

FIG. 20 is a cross section of an alternative optode having four optical fibers, suitable for use as a transmit optode in the optode-electrode positioning cap.

FIG. 21 is an exploded drawing illustrating components of the optode of FIG. 20.

DETAILED DESCRIPTION OF THE EMBODIMENTS

Component Parts

Figure 2A:
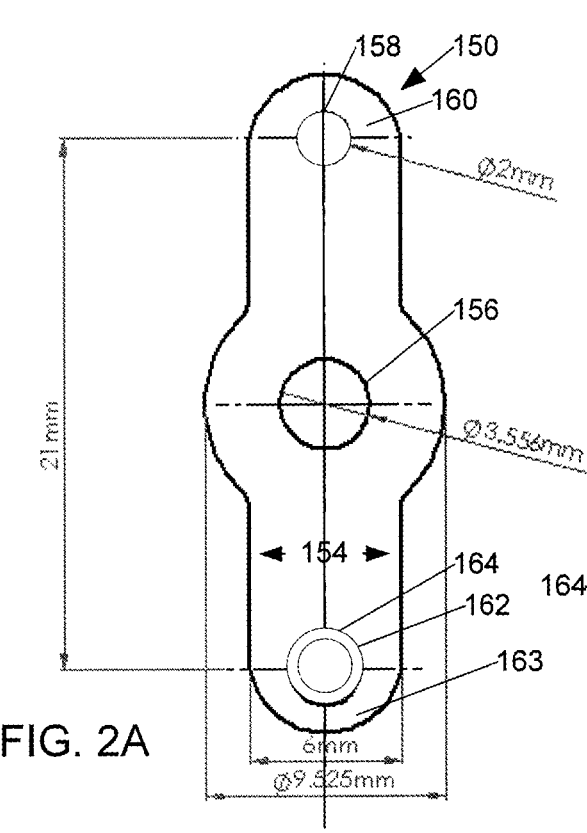
FIG. 2A is a top view of a double-ended semirigid link having a central hole for pivoting on the electrode of FIG. 1A.

An electrode 100 is illustrated in FIGS. 1A and 1B. In an embodiment, this electrode is machined from brass, in alternative embodiments the electrode may be fabricated from silver, stainless steel, titanium, aluminum, or another biocompatible corrosion-resistant electrically-conductive substance. The electrode has an axial hole 102, with in an embodiment is straight, and in an alternative embodiment is machined to have a larger diameter at a midpoint 104 than at top or stem end 106 so as to retain a coupling connector for attaching a wire. The electrode has a lower portion 108 of larger diameter than top end 106; lower portion 108 is bored out to form a boundary 110 of a cavity 112 having a larger diameter than the axial hole 102. Any dimensions shown on the figures are approximate, although they have been used for a prototype.

The top or stem end 106 has a tooth 114 for retaining it in within a pivot hole of a link, see below.

The cavity 112 of the electrode is filled with an electrically conductive gel or paste when the electrode is used.

In an alternative embodiment for a prototype, electrodes were fabricated by boring out electrically-conductive brass bolts.

Figure 2B:
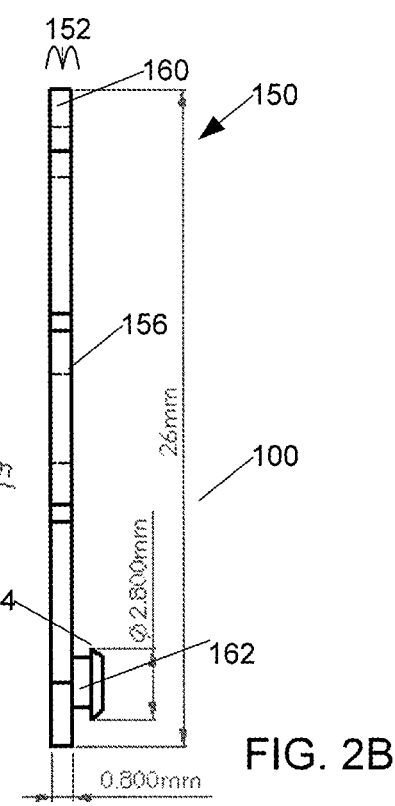
FIG. 2B is a side view of the semirigid link of FIG. 2A.
Figures 5A, 5B:
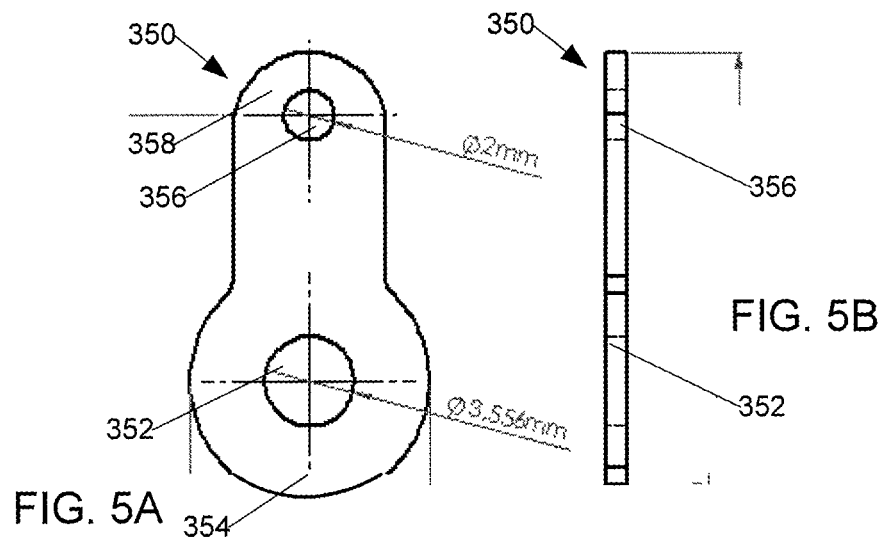
FIG. 5A illustrates a top view of a single-ended semirigid link having an end hole for pivoting on the electrode of FIG. 1A and an end hole.
FIG. 5B illustrates a side view of the single-ended semirigid link of FIG. 5A.

A semi-rigid link 150 is illustrated in FIG. 2A and FIG. 2B. In an embodiment the link is fabricated from a plastic, such as high molecular weight polyethylene (HMWPE) plastic, however in alternative embodiments the link may be fabricated from other plastics such as polypropylene, or other plastics. In a particular embodiment, links are cut from an acetyl copolymer sheet. The link is thin in one dimension 152 such that it may bend, however it is wide in an axis 154 perpendicular to the thin dimension in which it is rigid. The link is therefore semi-rigid in that it flexes in one axis 152, but does not flex in another axis 154. The link has a central hole 156 having dimensions such that the top or stem end 106 (FIG. 1B) of electrode 100 will fit within hole 156, and such that tooth 114 can retain electrode 106 within hole 156. Link 150 also has an end hole 158 in a first end portion 160. Link 150 also has a stud 162 in a second end portion 163. Stud 162 has a tooth 164 and has dimensions such that tooth 164 can retain stud 162 within end hole 158. Tooth 164 is shaped such that stud 162 can be forced or snapped into hole 158

In an embodiment, semi-rigid link 150 is fabricated by injection molding of the plastic, followed by drilling or punching of central hole 156 and end hole 158.

A semirigid, narrow link 200 having a central stud 212 is illustrated in FIGS. 3A and 3B. The narrow link 200 is thin in one dimension 202 such that it may bend, however it is wide in an axis 204 in which it is rigid, axis 204 is perpendicular to the thin dimension 202. The narrow link 200 is thin in one dimension 202 such that it may bend, however it is wide in an axis 204 perpendicular to the thin dimension in which it is rigid. The link is therefore semi-rigid in that it flexes in one axis 202, but does not flex in another axis 204. The link has a central peg 206. Narrow link 200 has an end hole 208 in a first end portion 210. Link 200 also has a stud 212. Stud 212 has a tooth 214 and has dimensions such that tooth 214 can retain stud 212 within end hole 208 or within end hole 158 of link 150 (FIG. 2A). Tooth 214 is shaped such that stud 212 can be forced or snapped into holes 208 or 158.

In an embodiment, semi-rigid narrow link 200 is fabricated by injection molding of the same plastic, followed by drilling or punching of end hole 208.

A semirigid, narrow link 220 having a central hole 222 is illustrated in FIG. 3C and FIG. 3D. Link 220 has a stud 224 resembling toothed stud 212 of the narrow link of FIG. 3A. The narrow link of FIG. 220 may be fabricated by injection molding of the same plastic, followed by drilling or punching of central hole 222 and end hole 226. In a particular embodiment, the narrow link 220 is made by molding plastic in the same mold as the link 200 of FIG. 3A, but stud 212 is drilled out leaving central hole 222.

Another semirigid link 300, as illustrated in 4A and 4B, resembles semirigid link 150 of FIG. 2A except that the end 160 having hole 158 has been removed; the remaining link 300 has a hole 302 in a wide end 304, and a toothed stud 306 in a narrower end 308.

Another semirigid link 350, as illustrated in 5A and 5B, resembles semirigid link 150 of FIG. 2A except that the end 163 having stud 162 has been removed; the remaining link 350 has a hole 352 in a wide end 354, and a hole 356 to fit toothed stud 306, 162 (FIGS. 2A, 2B, 4A, 4B) in a narrower end 358.

Figure 6:
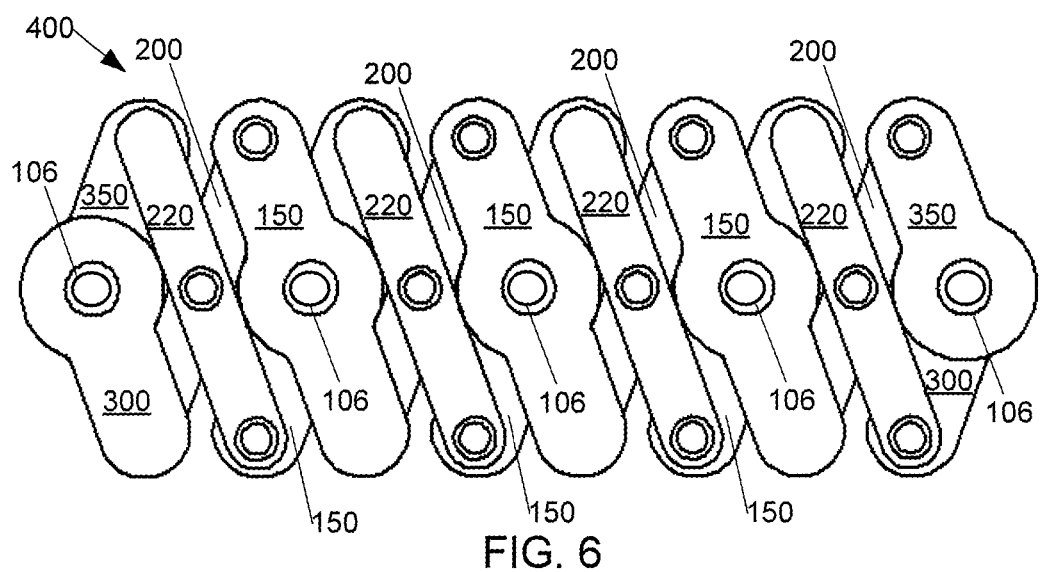
FIG. 6 is a top view of a linear, 5-electrode, subassembly.

The links 150, 200, 250, 300, 350, heretofore described are assembled with electrodes 100 (of which only top portion 106 is visible in FIG. 6) into telescoping electrode-positioning subassemblies 400 such as illustrated in FIG. 6. The subassemblies 400 are held together by snapping studs 162, 306, 212, 224 into end holes 356, 208, 226. The electrodes 100 are snapped into central holes 156 of wide semirigid links 100, serving as pivots for the wide semirigid links, and wide end holes 302, 352 of links 300, 350. Central studs 206 of narrow links 200 fit through central holes 222 of narrow links 220. These subassemblies may be assembled in any length, while FIG. 6 illustrates a 5-electrode subassembly; FIG. 7 is a bottom perspective view of a 4-electrode subassembly.

The subassemblies of FIGS. 6 and 7 are telescopic structures that may extend or compress as illustrated in FIGS. 8 and 8A. The coupled scissors action of the links pivoted on the electrodes acts to ensure that the electrodes maintain approximately even spacing as each subassembly extends or compresses. FIG. 8 illustrates subassemblies in retracted position. FIG. 8A illustrates subassemblies in extended position. However extended or retracted, the mechanical linkage of the links 150, 200, 250, 300, 350 of the subassemblies retains electrodes 100 at an even spacing throughout the subassembly. These subassemblies are therefore herein termed telescoping assemblies of semirigid links, these subassemblies are of adjustable length in one axis in the plane of the links, flex in an axis perpendicular to the plane of the links, and resist bending in a third axis in the plane of the links.

Figure 9:
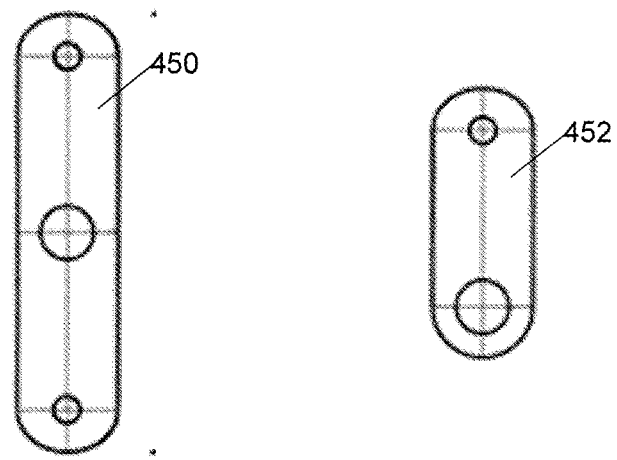
FIG. 9 illustrates alternative link shapes for use in the subassemblies of FIGS. 6 and 7.

Alternative embodiments of the subassemblies of FIGS. 6 and 7 may be assembled from links of differing shapes. For example, link 450 (FIG. 9) may in some embodiments substitute for link 150.

Figure 10:
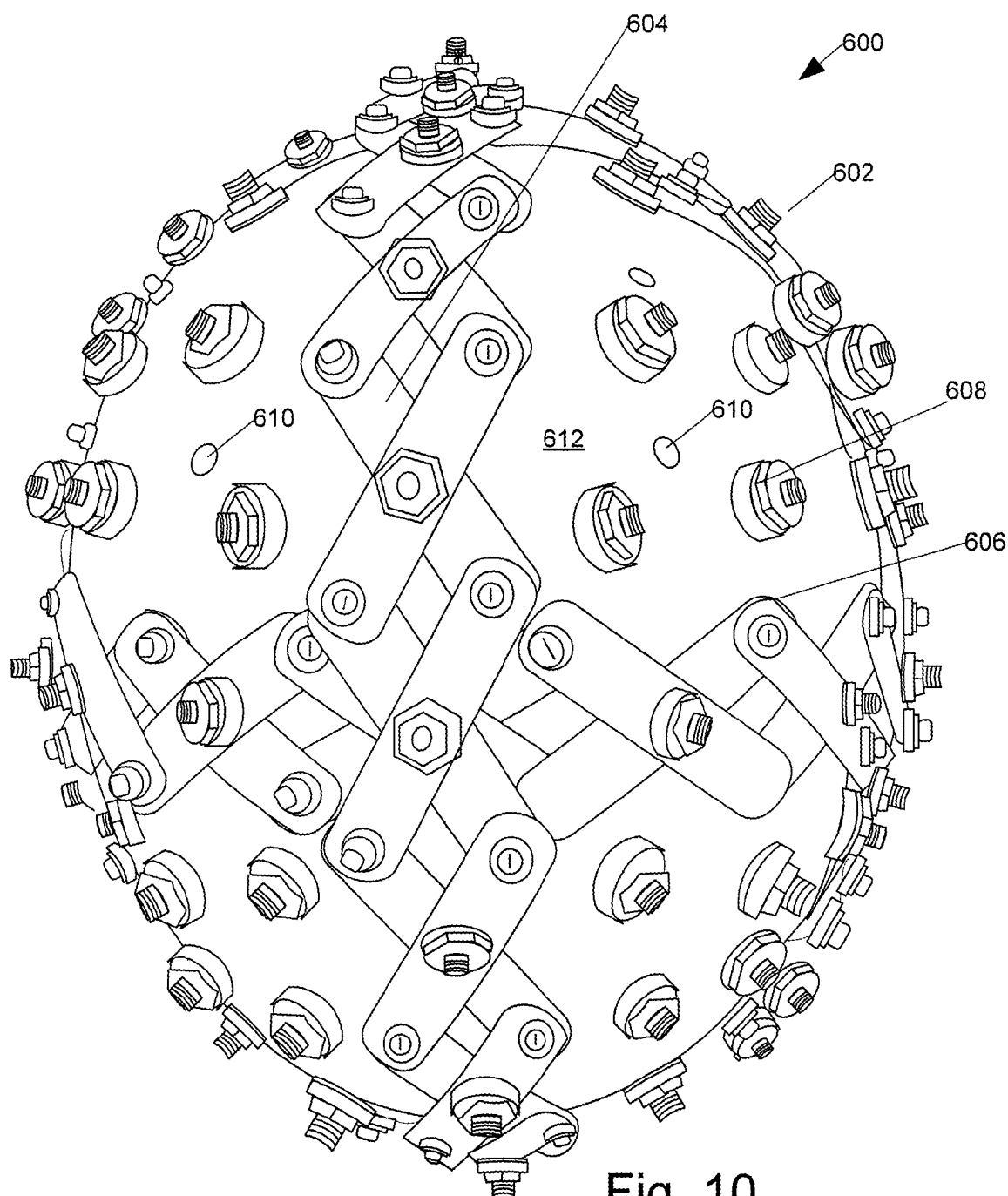
FIG. 10 is a top view of an electrode and optode positioning cap having subassemblies resembling those of FIGS. 6 and 7.

Subassemblies of the links and electrodes heretofore described are interconnected in the electrode positioning caps illustrated in FIGS. 10 and 11. In these caps, the semirigid subassemblies are pinned together at ends or intersections by electrodes serving as pins, in an embodiment of the cap 600, such as the embodiment of FIG. 10, the semirigid subassemblies form a circular headband 602 for positioning around a subject's head, an axial strap 604 running from the circular headband at the rear of the subject's head over the top of the head to attach to the circular headband at a point for positioning on a forehead of the subject. In this embodiment, another semirigid subassembly 606 runs across a top of the subject's head from the circular headband at a point for positioning near a left ear of the subject to the circular headband at a point for positioning near a right ear of the subject.

An electrode-optode positioning device, or cap, is illustrated in FIG. 10. This particular embodiment has sixty-five electrodes 608 (machined from brass bolts) located in a pattern derived from the 10-20 international electrode pattern. This embodiment has sixteen optodes (not shown in FIG. 10, although mounting holes 610 for some of the optodes are shown), and uses the alternative link embodiment illustrated in FIG. 9. In this embodiment, the cap is tensioned by an elastomeric membrane 612.

The electrode or optode positioning device, or cap, of FIG. 10 or FIGS. 11A, 11B, 11C, 11D, and 11E is formed of interconnected subassemblies of semirigid links that operate in scissors fashion on central pivots of intermediate links. The central pivots shown in these figures are electrodes; however in an alternative embodiment central pivots of intermediate links may be hinge pins or optodes. The subassemblies may extend or compress while maintaining approximately even spacing of the central pivots, and thereby maintains approximately even spacing of electrodes or optodes attached to the subassemblies.

Figure 11A:
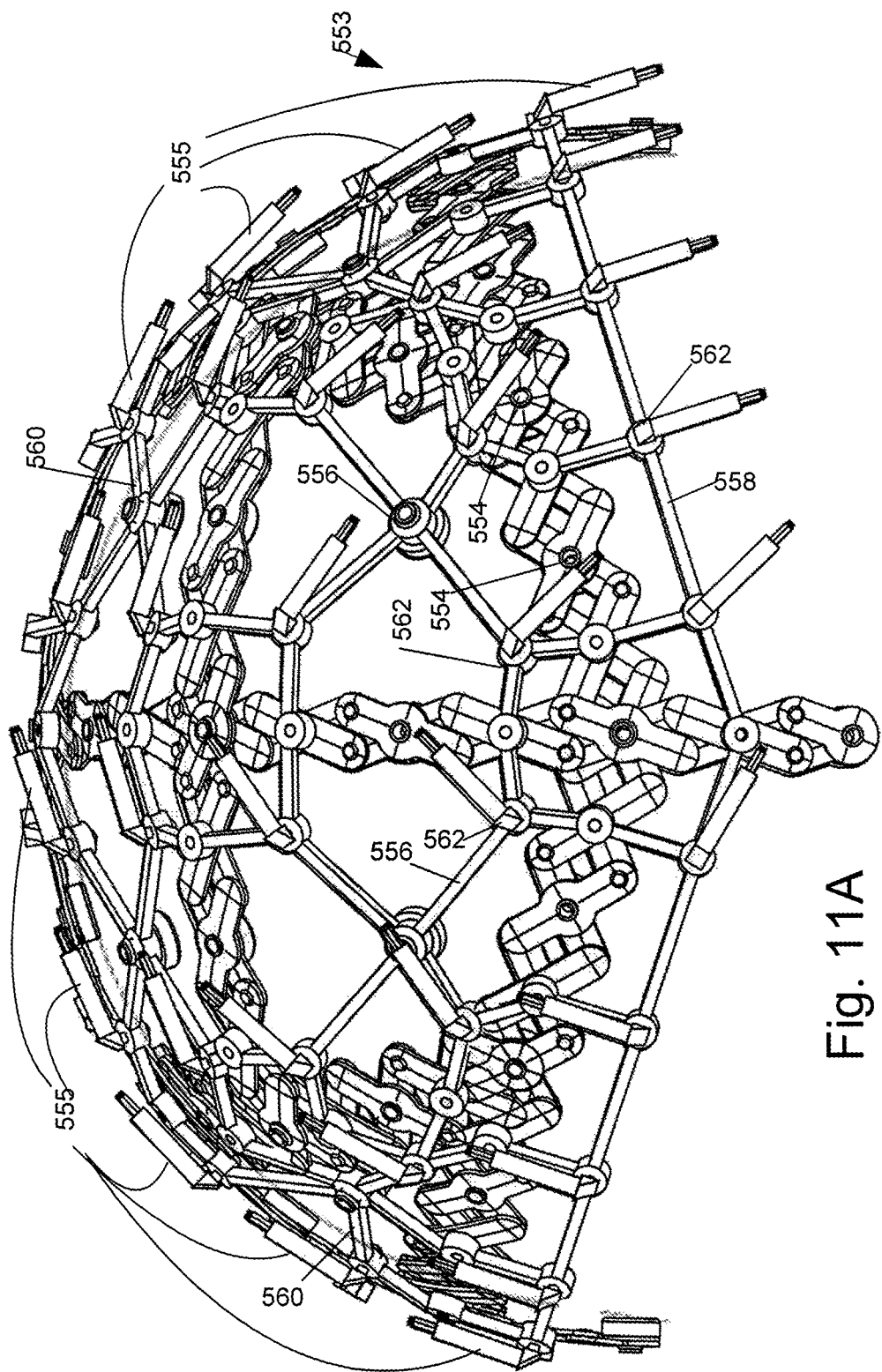
FIG. 11A is a side view of an alternative embodiment of an electrode and optode positioning cap having subassemblies resembling those of FIGS. 6 and 7, and a tensioner as illustrated in FIG. 12, for positioning 65 electrodes and 64 optodes.
Figure 11B:
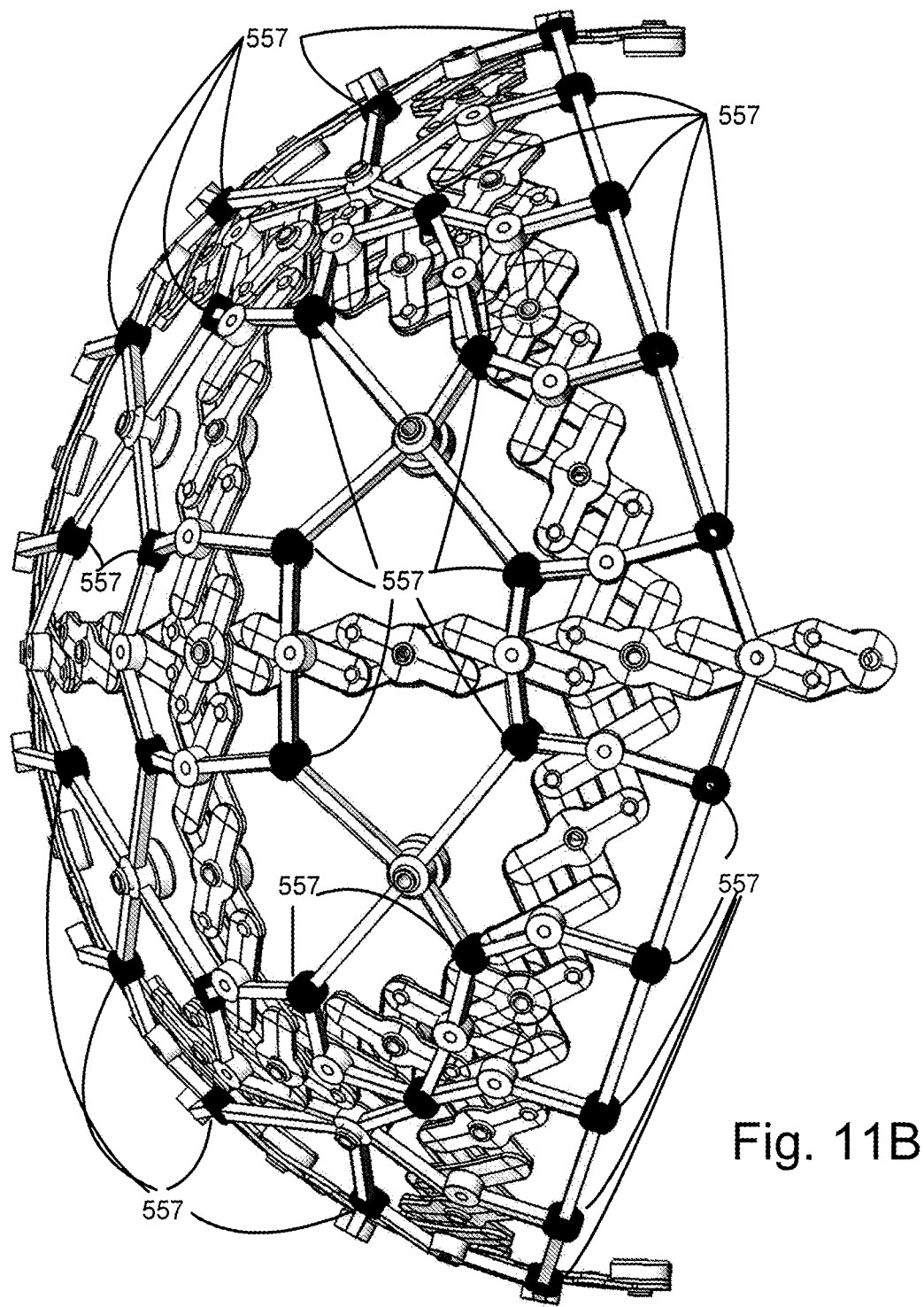
FIG. 11B is a side view of the embodiment of FIG. 11A, for positioning 65 electrodes and 64 optodes, with optodes deleted and black dots representing optode locations.
Figure 11C:
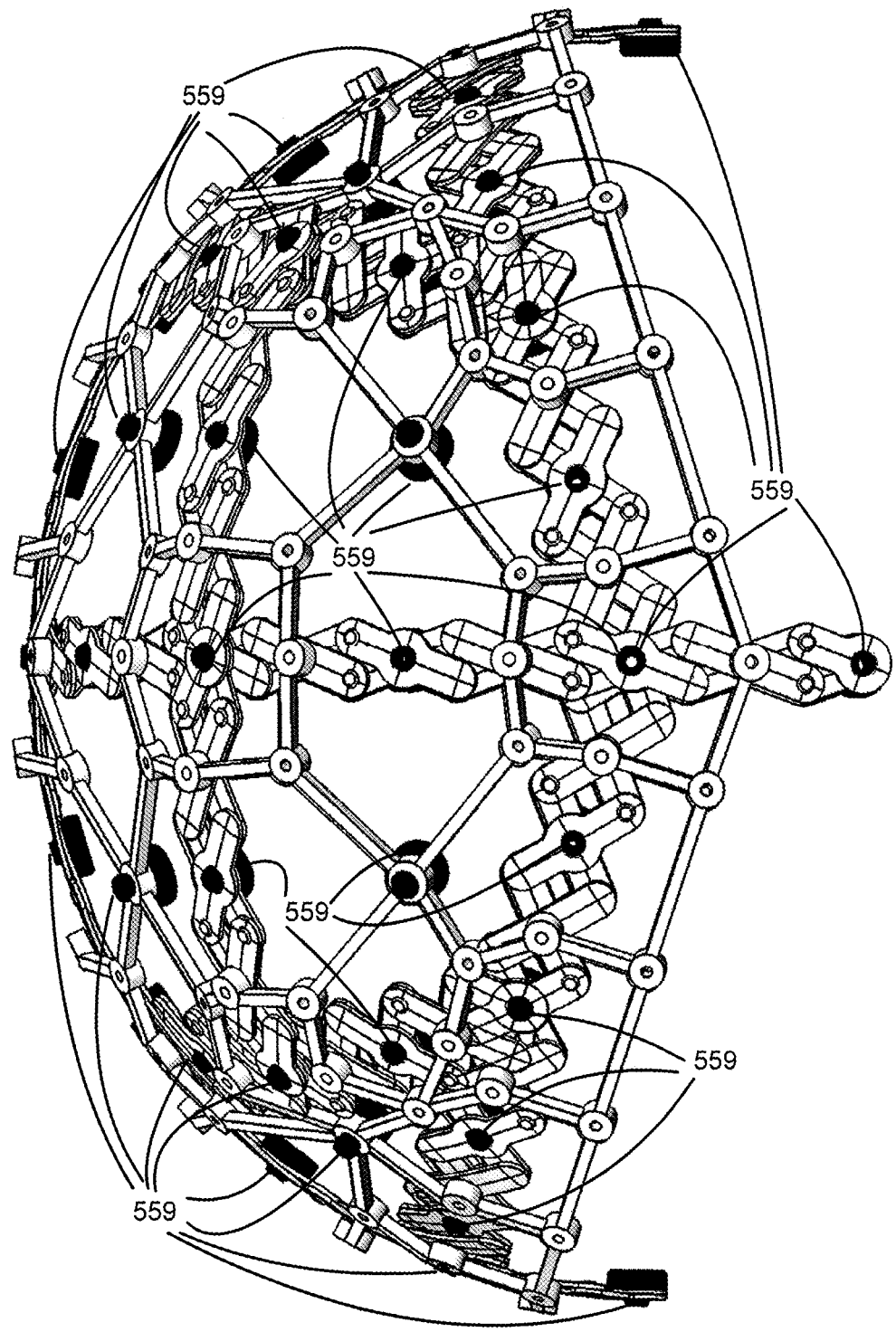
FIG. 11C is a side view of the embodiment of FIG. 11A with optodes deleted and black dots representing electrode locations.
Figure 11D:
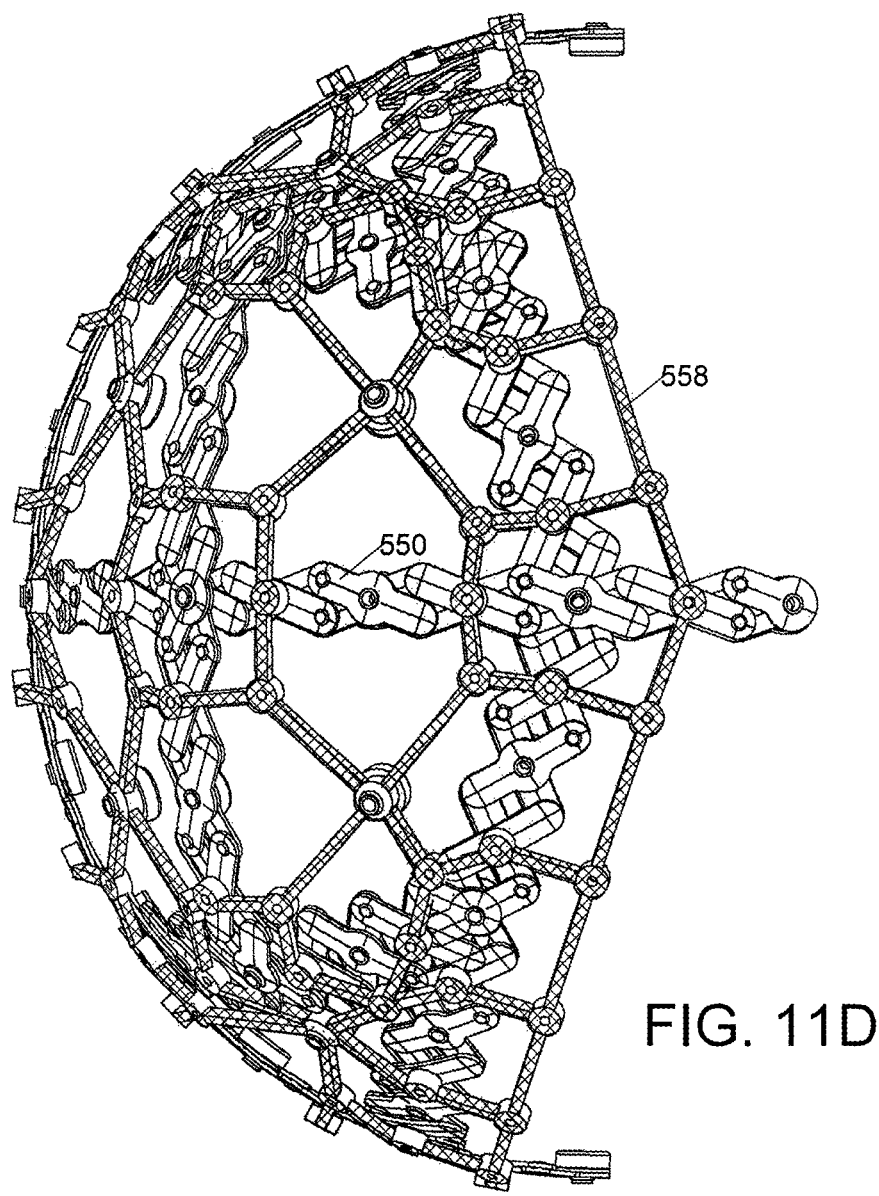
FIG. 11D is a side view of the embodiment of FIG. 11A with optodes removed to permit better viewing of the linkage and tensioning elastic, with tensioning elastic hatched for identification.
Figure 11E:
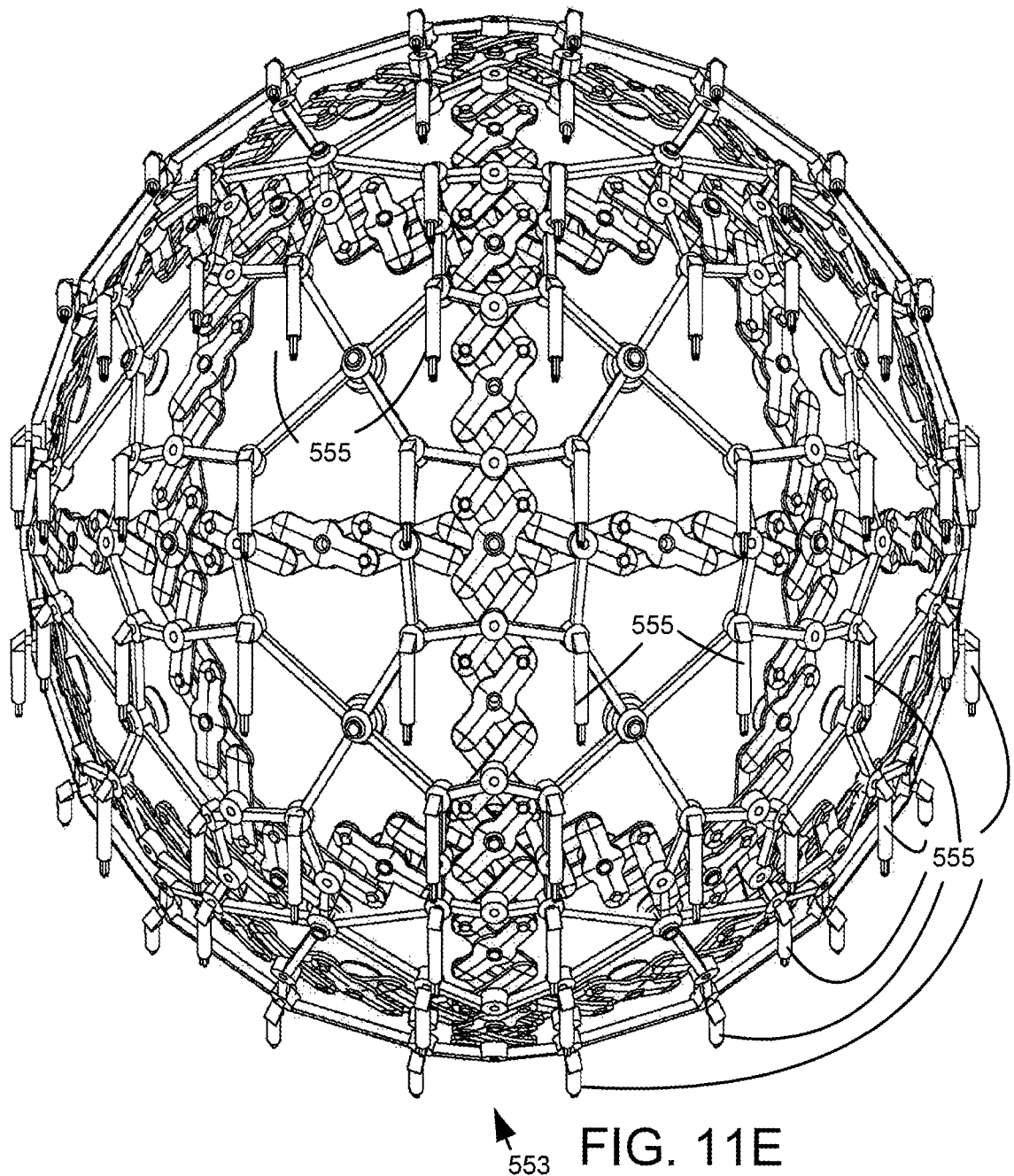
FIG. 11E is a top view of the embodiment of FIG. 11A.
Figure 12:
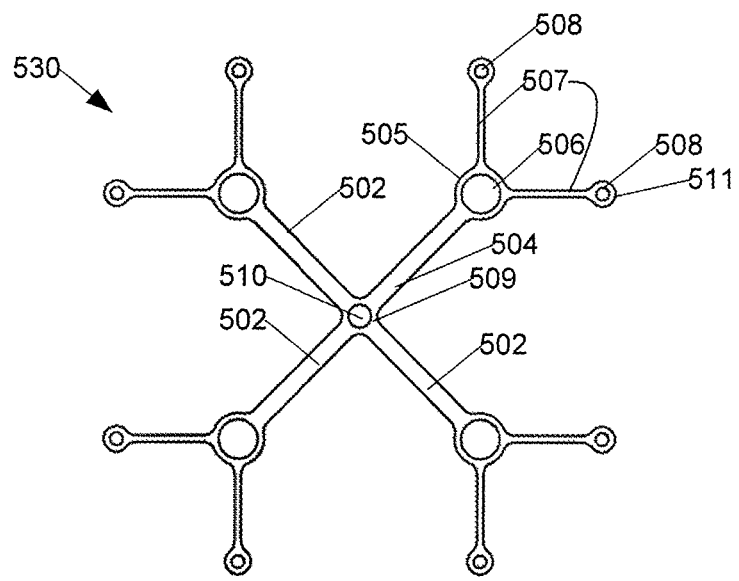
FIG. 12 is a top view of a tensioning elastic for use with the herein described subassemblies; the elastic is illustrated with dimensions as if under tension.

An alternative embodiment of the electrode-optode positioning device, or cap, is illustrated in FIGS. 11A, 11B, 11C, 11D, and 11E. FIG. 11A is a side view, FIG. 11E is a top view with optodes 555 present, but optode cables cut for simplicity. In this illustration, semirigid links 550, tensioners, and electrode positions 554 are illustrated. In addition to the 4-armed tensioners 556 (and as illustrated in FIG. 12), an elastic headband-tensioner 558 is provided to position some of the optodes and to help maintain position of the device on a subject's head. For simplicity, only some of the tensioners, links, electrode positions, optodes, and optode positions are marked on FIG. 11A. A chin-strap or harness, not shown, may also be provided for securing the optode-electrode positioning device or cap to a head of a subject in proper orientation. The optodes are oriented such that optical fibers associated with the optodes are directed towards a rear 553 of the electrode-optode positioning device where they may be bundled in a cable while providing minimal inhibition to movement of a subject wearing the device.

In FIG. 11B optode locations in elastomeric tensioners 556 are marked by black dots 557, and electrode positions are marked by black electrodes 559 in FIG. 11C.

The elastomeric tensioner 558 is illustrated in FIG. 11D as hatched shapes, and links 550 as unhatched shapes.

Figure 13:
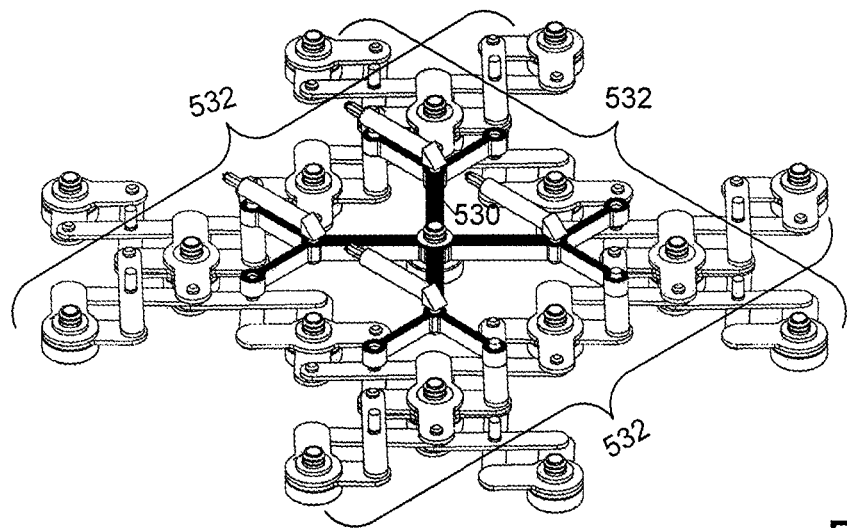
FIG. 13 illustrates the tensioning elastic of FIG. 12 framed by multiple electrode-link subassemblies in a molecule of an optode-electrode positioning cap.

In the caps, or optode electrode positioning devices of FIGS. 10 and 11A-11B, the semirigid subassemblies of links serve as stiffening and positioning-accuracy guaranteeing elements, while attached tensioning elastomer serves as a tensioning device to draw the electrodes and optodes into contact with a subject's scalp. In the embodiment of FIG. 10, the tensioning elastomer is elastomeric membrane 612. In the embodiment of FIG. 11A-11F, the tensioning elastomer is a web assembled from elastic sections including a tensioning elastic 530 of the type illustrated in FIG. 12, and interconnected between pegs 206 of narrow links 200 of multiple semirigid subassemblies 532 in a molecular pattern as illustrated in FIG. 13.

The tensioning elastic 530 of FIG. 12 has four arms 502, 504 each coupled to a central button 509 having a hole 510 for securing an electrode. Each arm 502, 504 extends from the central button to a lateral button 505 having a hole 506 for securing an optode. At the lateral button 505, each arm divides into a pair of branch arms 507. Each branch arm 507 terminates in a terminal button 511 having a hole 508 for securing to a peg 206 of a narrow link 200. In an embodiment, to encourage proper positioning of optodes by equalizing stretch in the arms and branch arms, branch arms 507 have half the cross sectional area of arms 502, 504.

Figure 12A:
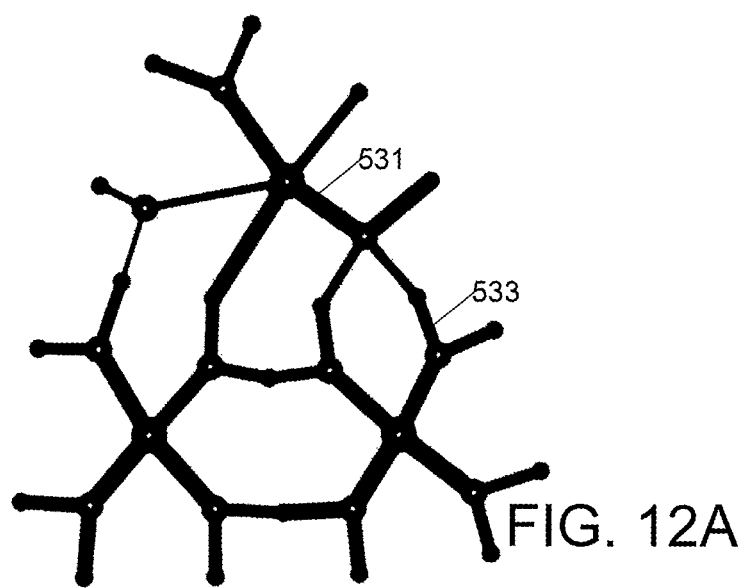
FIG. 12A is a perspective view illustrating the tensioning elastic of FIG. 12.

In an embodiment, the elastomeric tensioner 558 is fabricated as quadrants 531 (FIG. 12A) with one or more sections 533 as illustrated in FIG. 12. Each quadrant is fabricated by gluing multiple portions of elastomer together In order to provide proper coverage of the frontal regions above and to each side of the subject's eyes, an alternative tensioning elastic 560 may be used, and may appear in an appropriate quadrant. This alternative elastic 560 has five arms instead of the four arms of tensioning elastic 530, but only three of the arms have two branch arms, while the other two arms are straight arms with neither lateral buttons nor branch arms. These straight arms extend directly to pegs 206 on narrow links 200 of link subassemblies.

It has been found that not all human heads have the same shape. In order to allow for head crown height to be independently adjusted from head circumference, at selected decoupling joints the subassemblies of links are decoupled from one another. This decoupling is performed by having links of different subassemblies pivoted on the same electrode as links of other subassemblies, but not otherwise interacting with those subassemblies. For example, two subassemblies in line may be decoupled by using two short wide semirigid links of FIG. 4A or FIG. 4B for each subassembly, instead of using two wide semirigid links of FIG. 2A. Subassemblies that cross, for example at a crown of the device for positioning at the crown of a subject's head, may be decoupled by providing separate links for each subassembly.

Figure 14:
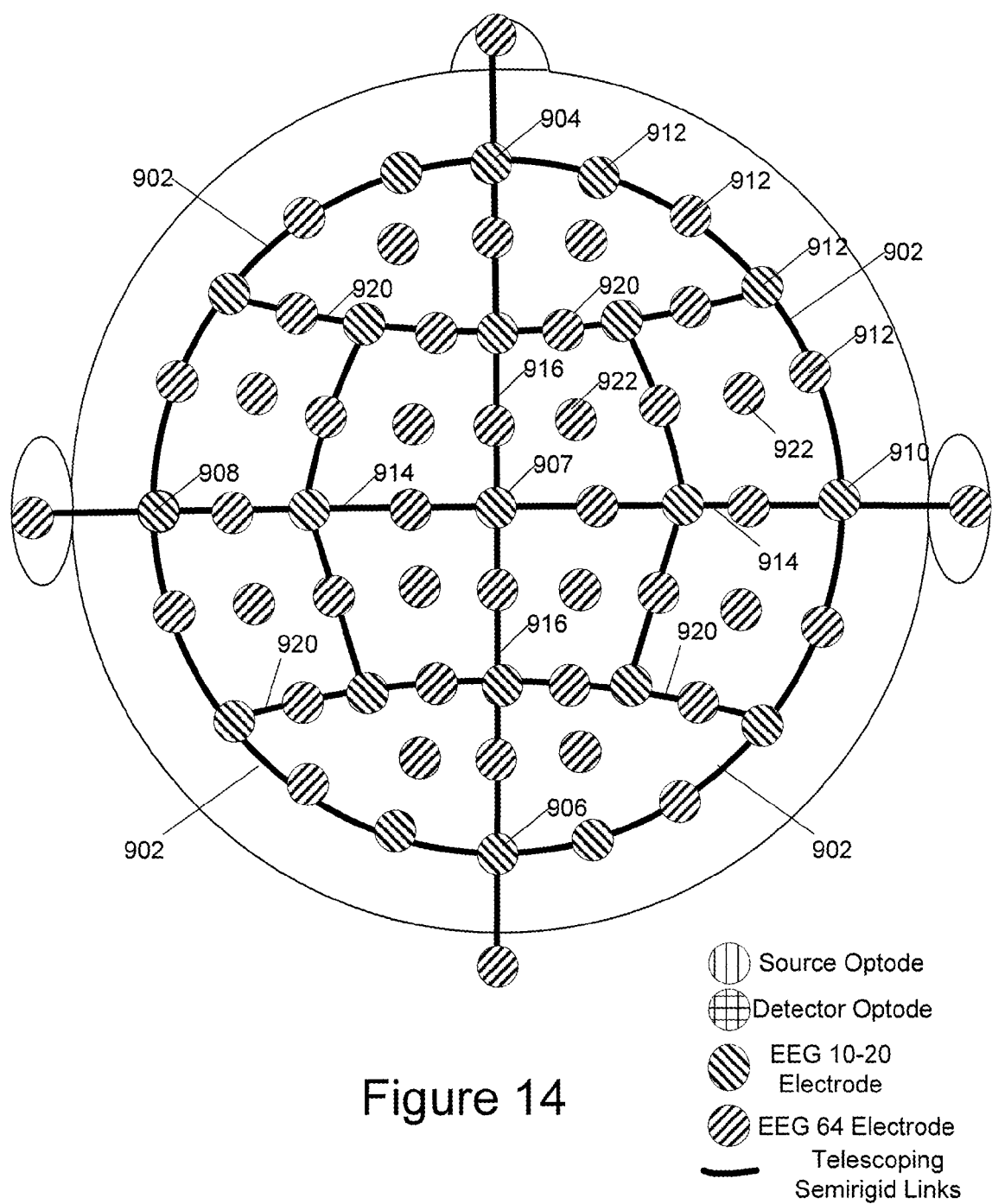
FIG. 14 illustrates an electrode placement pattern for use with 65 electrodes.

An exemplary layout of the electrode-optode positioning device of FIG. 11A-11E is illustrated schematically in FIG. 14. Four expandable or contractible subassemblies 902 of semirigid links are connected by center-forehead 904, back of head 906, left ear 908, and right ear 910 pivots, which in an embodiment are electroencephalographic electrodes. Pivots of each subassembly are electrodes 912, the subassemblies act to maintain even, or approximately equal, spacing between electrodes attached to each subassembly. An additional pair of subassemblies 914 act as a transverse bridge across the loop from left ear pivot-electrode 908 to right ear pivot-electrode 910, and another pair 916 act as a sagittal bridge from center-forehead pivot-electrode 904 to back of head pivot or electrode 906, thereby dividing the positioning device into quadrants; the transverse bridge and sagittal bridge are coupled at a crown pivot or electrode 907. A subset of electrodes 912 form a standard 10-20 pattern of electroencephalographic electrodes. A further four subassemblies form a bridge 920 from the loop to the sagittal bridge in each quadrant. Additional electrodes 922 are attached to the elastomeric tensioning device that is provided to tighten the positioning device about an object such as a subject's head.

Figure 14A:
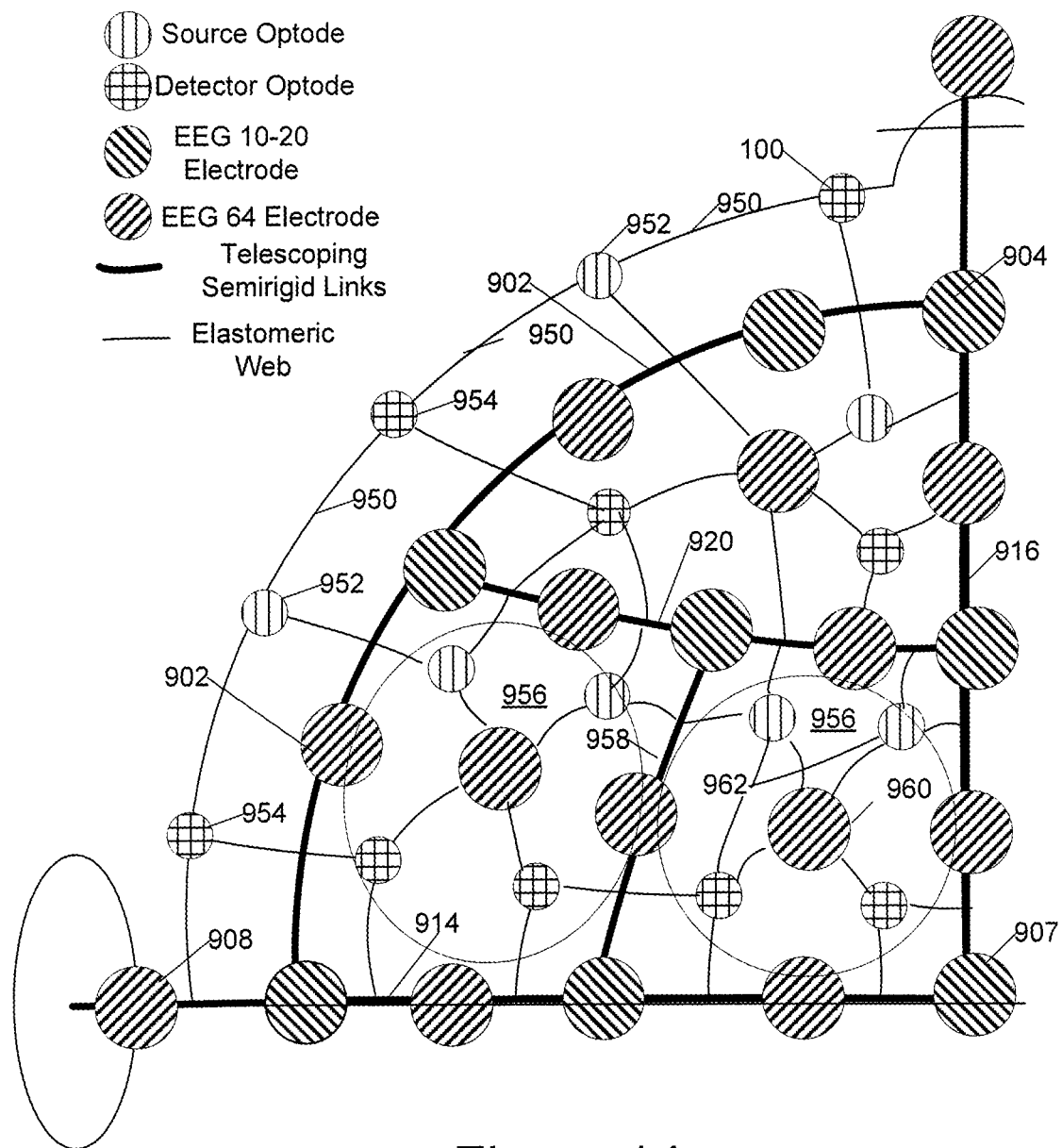
FIG. 14a illustrates one quadrant of an optode and electrode pattern for use with 64 optodes and 65 electrodes.

The optode and elastomeric web interconnections of a quadrant of the embodiment of FIG. 14 are illustrated in FIG. 14a. A plurality of elastomeric links 950 between alternately transmit optodes 952 and receive optodes 954 form a loop below and outside the loop formed of semirigid links 902, a plurality of optodes being secured to the elastomeric links.

The web further has a four-armed tensioning elastic, with each arm forked, as described with reference to FIG. 12, at 956, coupling to eight points on sagittal bridge 916, bridge 920, and transverse bridge 914, as well as to a short bridge 958 between bridge 920 and transverse bridge 914 to provide tension to the cap. An electrode and four optodes are mounted to the four-armed tensioning elastic.

Figure 15:
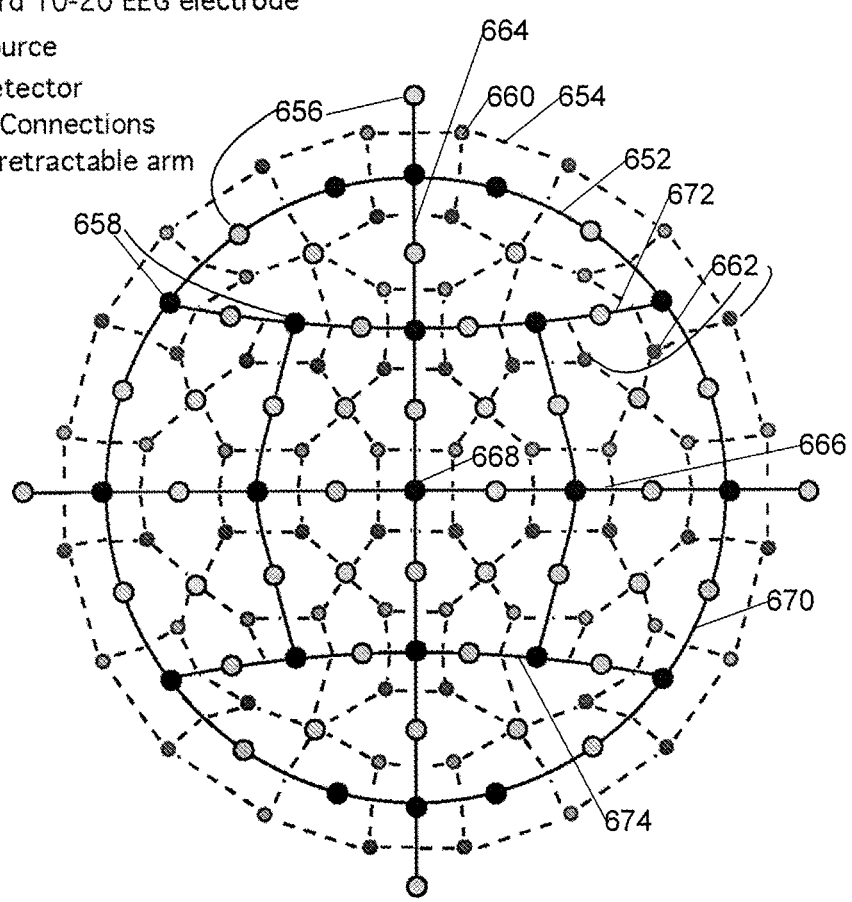
FIG. 15 is a schematic diagram illustrating an electrode and optode placement pattern for use with 64 optodes and 65 electrodes, also illustrating tensioner and semirigid link placements.
Figure 16:
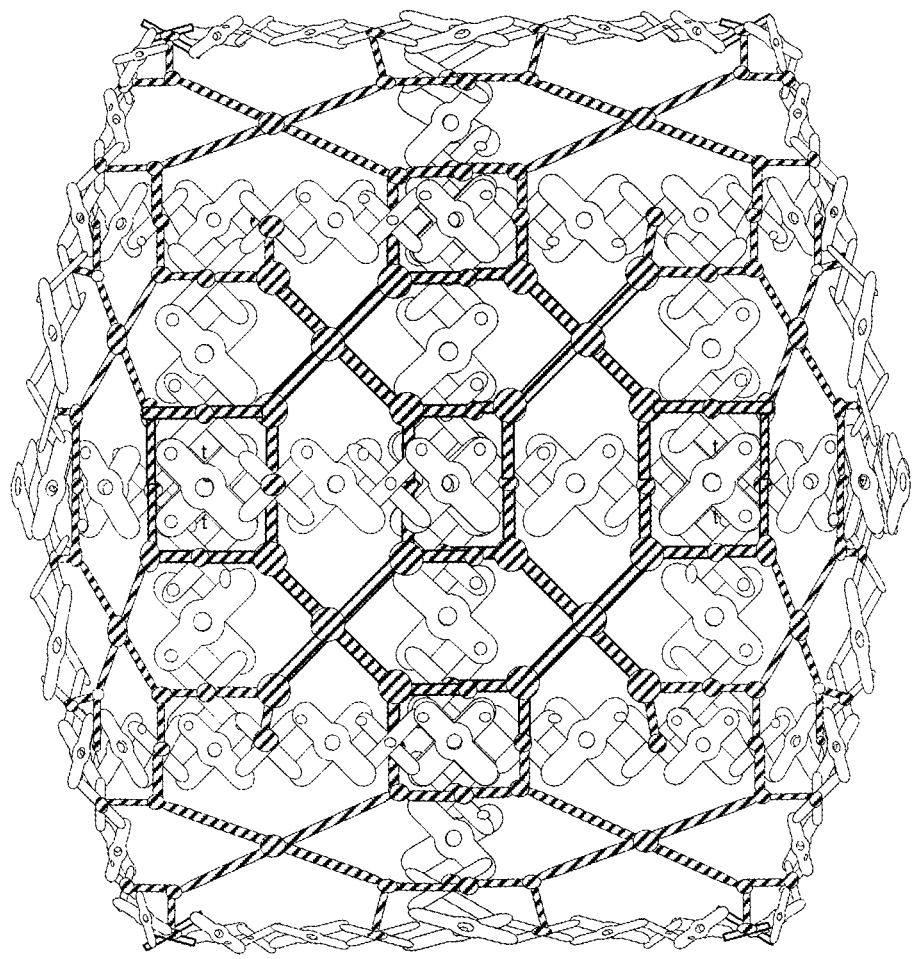
FIG. 16 is an approximate illustration of a cap implementing the schematic of FIG. 15 with electrodes, optodes, optical fibers and wiring removed.

An electrode-optode pattern for 65 electrodes and 64 optodes is illustrated schematically in FIG. 15. In this schematic, solid lines 652 represent mechanical connections between optodes and electrodes formed by semirigid telescopic subassemblies of semirigid links as heretofore described. Similarly, dashed lines 654 represent mechanical connections between optodes and electrodes formed by tensioning elastics such as elastics 558, 556, and 560 (FIG. 11B). Large circles, including solid circles 658 (representing electrodes of the 10-20 standard pattern) and yellow-filled circles 656 (representing additional electrodes in the 65-electrode pattern) represent electroencephalographic electrodes. Small circles, including blue-centered circles 660 and red-centered circles 662, represent optodes. Sagittal semirigid telescopic subassembly 664 is decoupled from, but hinged to the same electrode as, coronal semirigid telescopic subassembly 666 at the crown 668 of the cap. Similarly, headband semirigid telescopic subassembly 670 is decoupled from, although hinged at the same electrode as, the sagittal 664 and coronal 666 semirigid telescopic subassemblies where those subassemblies intersect. Similarly, decoupling occurs at intersections of anterior coronal subassembly 672 and posterior coronal subassembly 674 with the headband subassembly 670. In use, all electrodes are typically coupled to electroencephalographic apparatus for monitoring electrical activity in the brain of a subject to whom the cap is attached. In a particular embodiment, when in use blue-centered circles 660 represent optodes coupled to photodetector apparatus, and red-centered circles 662 represent optodes coupled to light sources, for performing diffuse optical imaging of brain oxygenation and functional neuroimaging of the subject; in alternative embodiments all optodes may be coupled through beamsplitters to both photodetector apparatus and light sources.

Figure 17:
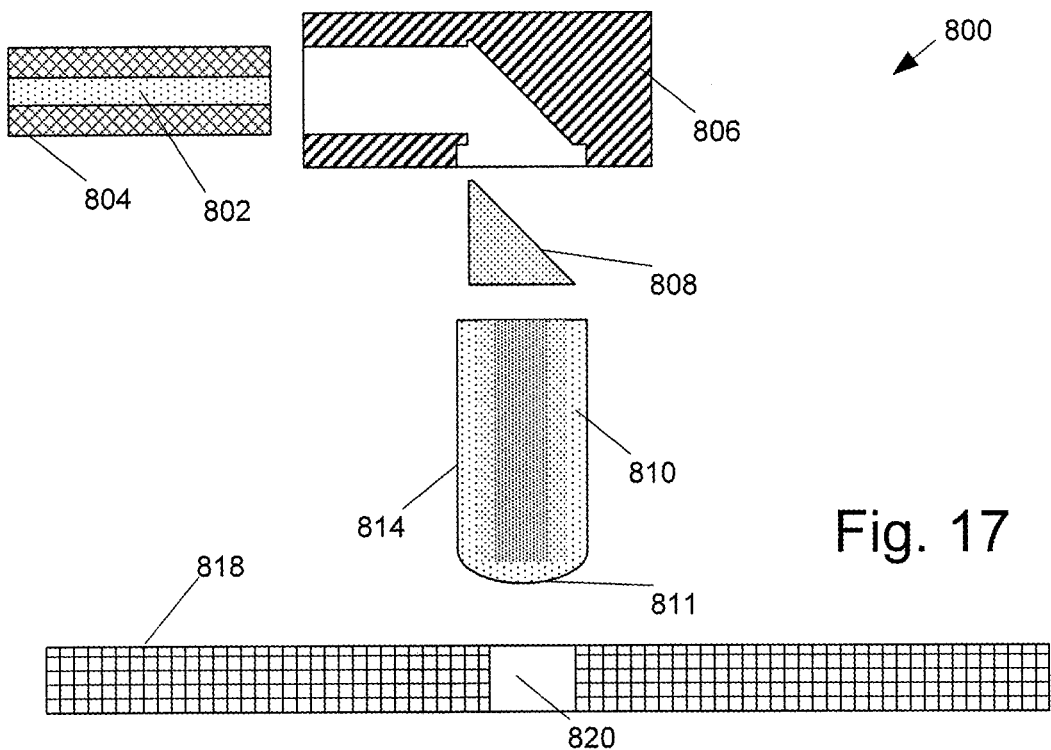
FIG. 17 is an exploded cross-section illustration of an embodiment of an optode for use in an optode-electrode positioning cap.
Figure 18:
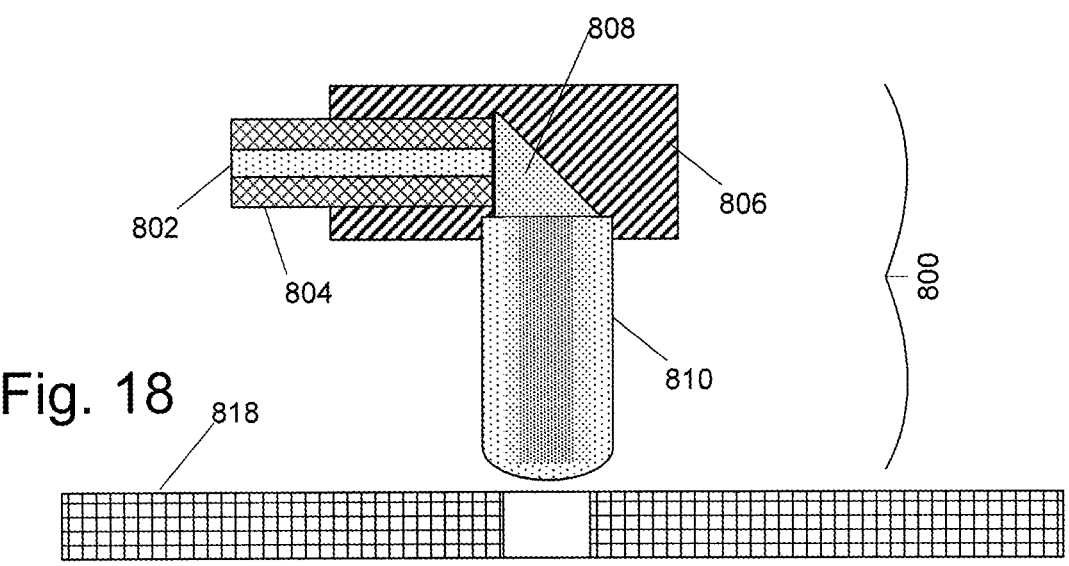
FIG. 18 is a cross-section illustration of the embodiment of an optode of FIG. 17, with the optode assembled and prepared for insertion into an optode-electrode positioning cap.

The optode 800 of FIGS. 17, 18, and 19 has a fiber optic fiber or fiber bundle 802 as known in the art of fiber optics and as suitable for transmitting light of a desired wavelength. The optic fiber may have a jacket 804 and is inserted into and attached by glue or a collet into an optode body 806. Optical fiber 802 is optically coupled to a prism 808 also mounted within the optode body 806, and prism 808 is coupled to the high-density central portion of a flat end of a graded-index (GRIN) lens 810. GRIN lens has a convex curved end 811 for optical coupling to a scalp of a subject.

The GRIN lens 810 is also attached to the optode body 806, and has an outer circumferential surface 814.

An elastomeric element 818, such as an elastomeric tensioner 558, has holes 820 having diameter small enough to grip the circumferential surface 814 of the GRIN lens 810.

In use, GRIN lens 810 of each optode is inserted into a hole 820 of the associated elastic element 818, as shown in FIG. 6; the cap is then secured to the head of a subject such that the convex surface or curved end 811 of each optode is held adjacent to the scalp of a subject (not shown), and the optical fiber 802 is coupled to an appropriate light source or light measurement device.

In an alternative embodiment of the transmit optode 850, a barrel 852 is formed from a fifteen-millimeter section of brass rod by drilling a cavity 856 along an axis of the rod with a number 50 drill approximately half-way along the length of the section of rod, and a cavity 854 is formed by drilling with a number 59 drill for the remainder of the section of rod. For receive optodes, a barrel 852 is formed from 15 millimeter section of brass rod by drilling a cavity 856 along an axis of the rod with a number 59 drill approximately half-way along the length of the section of rod, and cavity 854 is formed by drilling with a number 69 drill for the remainder of the section of rod.

Once cavities 854 are formed, jacket 860 is stripped from an end of a single optical fiber 858 for receive optodes, and for transmit optodes jacket 860 is stripped from an end of each of four optical fibers 858. The ends of the optical fibers are inserted through cavity 856 into cavity 854 and jacket 860 is cemented into cavity 856. Fiber ends are then cut and polished flush with an end 868 of barrel 852. A prism 862 is then cemented to the end 868 of barrel 852. The prism being optically coupled to the optical fibers, to direct light at a 90 degree angle into a graded-index lens cylinder 864, a first end of which is cemented and optically coupled to the prism 862. A hemispherical interface lens 866 is then cemented and optically coupled to a second end of cylinder 864. A diameter of hemispherical lens 866 is greater than that of barrel 852, and barrel 852 has length approximately equal to a thickness of tensioning elastic web 531. The optodes are then snapped into holes in tensioning elastic web 531 at each optode location illustrated with reference to FIG. 11B such that hemispherical lens 866 retains the optodes in the holes.

Figure 22:
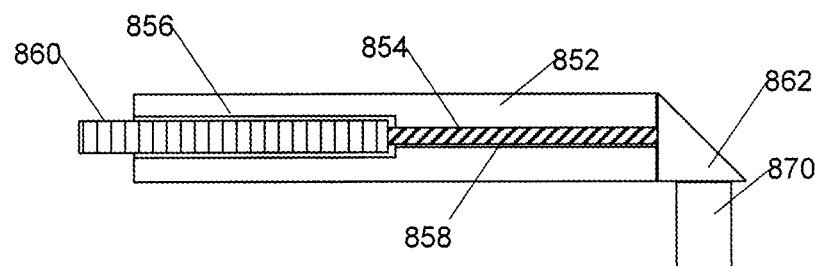
FIG. 22 is an illustration of an alternative optode having a drum lens.

An alternative optode is illustrated in FIG. 22. In this embodiment, the cylindrical GRIN lens 864 and hemispherical lens 866 of the optode illustrated in FIG. 20 are replaced by a short transparent drum lens 870, other components of the optode remain as discussed with reference to FIGS. 20 and 21. As with the optodes of FIGS. 20 and 21, the alternative optode of FIG. 22 is produced in a single-fiber (shown) receive version and in a quadruple-fiber transmit version. To enhance retention of the optode of FIG. 22 in a hole of elastic tensioning web, glue may be placed between barrel 852 and an upper surface of the web. In an embodiment where the elastomeric tensioning web is thin, drum 870 is short, it is of a homogeneous material. In an alternative embodiment where drum lens 870 is longer because the web is thicker, drum lens 870 may be a graded index drum lens formed of transparent material having a higher index of refraction in its center than towards sides of the drum shape.

In a system for performing diffuse optical imaging and electroencephalography, each of the four fibers from each transmit optode is coupled to a light source of a diffuse-optical imaging system that is operable at one of four specific wavelengths or four narrow wavelength bands. The fiber from each receive optode is coupled to a photodetector of the diffuse optical imaging system, such that light propagating along paths through a subject's head tissue from each transmit optode to an adjacent receive optode can be measured by the diffuse-optical imaging system.

The combined electrode—optode positioning cap herein described is adaptable to diffuse-optical imaging alone by replacing the electrodes at pivot points with hinge-pins. Similarly, the electrode—optode positioning cap is adaptable for use in electroencephalography alone by removing the optodes.

In an alternative embodiment for use where overall height of the electrode-optode positioning device is greatly restricted and where some electrode and/or optode placement error can be tolerated, most or all electrodes and the semirigid telescopic structures are removed so that the elastomeric tensioning web is used with optodes for diffuse-optical imaging alone, or for combined electrode-optode with a small number of electrodes placed in the web.

Figure 23:
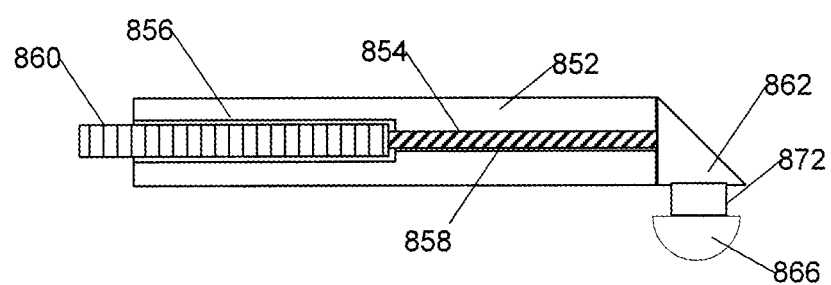
FIG. 23 is an illustration of an alternative optode having a short transparent spacer and hemispherical lens.

An alternative optode for use with thin webs and where height is restricted is illustrated in FIG. 23. While the cylindrical GRIN lens 864 of the optode illustrated in FIG. 20 may be of any length, the focusing effect of the GRIN lens is not necessary where it can be very short because the web tensioning element is very thin. In the alternative optode of FIG. 23 the GRIN lens is replaced by a short transparent spacer 872, other components remain as discussed with reference to FIGS. 20 and 21. As with the optodes of FIGS. 20 and 21, the alternative optode of FIG. 23 is produced in single-fiber (shown) receive version and in a quadruple-fiber transmit version.

It is desirable to combine diffuse optical imaging and electroencephalography obtained through electrodes and optodes secured in the herein described electrode and optode positioning device or cap to provide data indicative of brain function, this data can provide functional neuroimaging data at far less equipment cost, bulk, and weight than prior-art functional nuclear Magnetic Resonance Imaging (fMRI). It is expected that, with electrodes and optodes firmly held in desired positions despite subject activity, functional neuroimaging may be possible of subjects performing such activities as walking on a treadmill or engaging in social activities that are not possible with fMRI. Such functional neuroimaging is expected to be greatly useful in research as well as in the diagnosis and treatment monitoring of psychiatric and neurological disorders.

In an embodiment, the electrode and optode positioning cap including the elastomeric tensioning web and the plastic semirigid links, the attached optodes with their optical fibers, and the attached electrodes are fabricated from nonmagnetic materials compatible with magnetic resonance imaging (MRI) and magnetoencephalography (MEG) to permit calibration and comparison of infrared diffuse optical and electroencephalographic functional neuroimaging obtained through the electrodes and optodes with fMRI or MEG functional neuroimaging. In an embodiment, the optode-electrode positioning cap is used for simultaneous fMRI, electroencephalography, and infrared diffuse-optical functional neuroimaging; and in an alternative embodiment the optode-electrode positioning cap is used for simultaneous MEG, electroencephalography, and infrared diffuse-optical functional neuroimaging.

Various combinations and anticipated embodiments of the positioning cap are anticipated, including embodiments as follows:

An embodiment designated A having at least one semirigid telescopic structure forming at least one loop, the semirigid telescopic structure capable of extension and compression while maintaining even spacing of devices selected from the group consisting of optodes and electrodes attached thereto; and an elastomeric tensioning device configured to tighten the semirigid telescopic structure around an object.

An embodiment designated B of the embodiment designated A further comprising at least one semirigid telescopic structure forming a bridge across the loop.

An embodiment designated C of the positioning cap designated A or B further comprising at least one semirigid telescopic structure forming a sagittal bridge across the loop.

An embodiment designated D of the positioning cap designated B or C wherein the semirigid telescopic structures comprise a plurality of links and pivots, and wherein a plurality of devices selected from the group consisting of optodes and electrodes serve as pivots of the telescopic structures.

An embodiment designated E of the positioning cap designated D wherein the plurality of devices that serve as pivots are electrodes and a plurality of the electrodes are positioned according to the 10-20 pattern.

An embodiment designated F of the positioning cap designated D or E wherein the elastomeric tensioning device is an elastomeric membrane.

An embodiment designated G of the positioning cap designated D or E wherein the elastomeric tensioning device is a web, the web having a plurality of links that form an outer loop.

An embodiment designated H of the positioning cap designated G wherein a plurality of optodes are attached to the outer loop.

An embodiment designated I of the positioning cap designated G or H wherein the web further comprises at least one four-armed tensioning elastic portion, where each arm of the four-armed tensioning elastic portion has a forked end, each forked end attached to a semirigid telescopic structure.

An embodiment designated J of the positioning cap designated I wherein an electrode and a plurality of optodes are attached to the four-armed tensioning elastic portion.

A positioning cap designated K comprising the positioning cap designated B, C, D, E, F, G, H, J or I wherein a plurality of the optodes are coupled to light sources of a diffuse optical imaging system, and a plurality of the optodes are coupled to photosensors of the diffuse optical imaging system, the diffuse optical imaging system configured to perform functional neuroimaging.

A positioning cap designated L comprising the positioning cap designated A, B, C, D, E, F, G, H, I, J, or K further comprising at least one optode having a barrel cemented to a jacket of an optical fiber, the optical fiber coupled to a prism, the prism coupled to a graded-index lens, and the graded-index lens coupled to a hemispherical lens.

The positioning cap designated L wherein the barrel of at least one optode is cemented to jackets of a plurality of optical fibers, the plurality of optical fibers coupled to the prism.

An optode designated M having a barrel cemented to a jacket of an optical fiber, the optical fiber coupled to a prism, the prism coupled to a graded-index lens oriented at a right angle to the barrel, and the graded-index lens coupled to a hemispherical lens.

A positioning device designated N comprising a plurality of the optodes designated M inserted into holes of an elastomeric web.

A positioning device designated P comprising the positioning device designated N further comprising at least one electroencephalographic electrode.

A positioning device designated Q comprising the positioning device designated N or P further comprising at least one semirigid telescopic structure attached to the elastomeric web at multiple points and forming at least one loop, the semirigid telescopic structure capable of extension and compression while maintaining even spacing of devices attached thereto.

A method of stably and repeatably positioning a plurality of devices selected from the group consisting of electrodes and optodes designated R on a subject's head includes attaching semirigid telescopic structures to an elastomeric tensioning device; attaching a plurality of devices selected from the group consisting of electrodes and optodes to the elastomeric tensioning device; attaching a plurality of devices selected from the group consisting of electrodes and optodes to the semirigid telescopic structures; and placing the elastomeric tensioning device on a subject's head.

The method designated R wherein the semirigid telescopic structures comprise a plurality of arms each having a central hole, and wherein a plurality of the arms pivot on electrodes.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A positioning cap comprising:
   at least one semirigid telescopic structure forming at least one loop, the semirigid telescopic structure capable of extension and compression while maintaining even spacing of devices selected from the group consisting of optodes and electrodes attached thereto;
   wherein the semirigid telescopic structures comprise a plurality of telescoping subassemblies, each telescoping subassembly comprising a plurality of links and pivots with a first sub-portion between a first pivot and a second pivot of that subassembly, and a second sub-portion between the first pivot and a third pivot of that subassembly, and wherein a plurality of devices selected from the group consisting of optodes and electrodes serve as the first, second, and third pivots of the telescopic structures; and wherein adjustment of a distance between the first and second pivot of each subassembly mechanically determines a distance between the first and third pivot of that subassembly; and
   an elastomeric tensioning device configured to tighten the semirigid telescopic structure around an object.

2. The positioning cap of claim 1 further comprising at least one semirigid telescopic structure forming a bridge across the loop.

3. The positioning cap of claim 2 wherein a plurality of the pivots are center pivots each located at a center of at least two links, and a plurality of the pivots are located at an end of at least two links, and where the devices selected from the group consisting of the optodes and electrodes comprise at least some of the center pivots.

4. The positioning cap of claim 2 further comprising at least one semirigid telescopic structure forming a sagittal bridge across the loop.

5. The positioning cap of claim 4 wherein the semirigid telescopic structures comprise a plurality of links and pivots, and wherein a plurality of devices selected from the group consisting of optodes and electrodes serve as pivots of the telescopic structures.

6. The positioning cap of claim 5 wherein the web further comprises at least one four-armed tensioning elastic portion, where each arm of the four-armed tensioning elastic portion has a forked end, each forked end attached to a semirigid telescopic structure.

7. The positioning cap of claim 5 wherein the plurality of devices that serve as pivots are electrodes and a plurality of the electrodes are positioned according to the 10-20 pattern.

8. The positioning cap of claim 7 wherein the elastomeric tensioning device is a web, the web having a plurality of elastomeric links that form an outer loop.

9. The positioning cap of claim 8 wherein a plurality of optodes are attached to the outer loop.

10. The positioning cap of claim 9 wherein the web further comprises at least one four-armed tensioning elastic portion, where each arm of the four-armed tensioning elastic portion has a forked end, each forked end attached to a semirigid telescopic structure.

11. The positioning cap of claim 10 wherein an electrode and a plurality of optodes are attached to the four-armed tensioning elastic portion.

12. The positioning cap of claim 11 wherein a plurality of the optodes are coupled to light sources of a diffuse optical imaging system, and a plurality of the optodes are coupled to photosensors of the diffuse optical imaging system, the diffuse optical imaging system configured to perform functional neuroimaging.

13. The positioning cap of claim 11 further comprising at least one optode having a barrel cemented to a jacket of an optical fiber, the optical fiber coupled to a prism, the prism coupled to a graded-index lens, and the graded-index lens coupled to a hemispherical lens.

14. The positioning cap of claim 13 wherein the barrel of at least one optode is cemented to jackets of a plurality of optical fibers, the plurality of optical fibers coupled to the prism.

15. The positioning cap of claim 5 wherein the elastomeric tensioning device is an elastomeric membrane.

16. A method of stably and repeatably positioning a plurality of devices selected from the group consisting of electrodes and optodes on a subject's head comprising:
   providing a plurality of semirigid telescopic structures attached to an elastomeric tensioning device; each telescoping structure comprising a plurality of links and pivots with a first sub-portion between a first pivot and a second pivot of that structure, and a second sub-portion between the first pivot and a third pivot of that structure, and wherein at least some of the plurality of devices selected from the group consisting of optodes and electrodes serve as the first, second, and third pivots of the telescopic structures; and wherein determining a distance between the first and second pivot of each subassembly determines a distance between the first and third pivot of that structure;

providing a plurality of devices selected from the group consisting of electrodes and optodes attached to the semirigid telescopic structures; and placing the elastomeric tensioning device on a subject's head.

* * * * *

UNITED STATES PATENT AND TRADEMARK OFFICE
CERTIFICATE OF CORRECTION

| | | |
|---|---|---|
| PATENT NO. | : 8,948,849 B2 | Page 1 of 1 |
| APPLICATION NO. | : 13/863183 | |
| DATED | : February 3, 2015 | |
| INVENTOR(S) | : Solomon G. Diamond et al. | |

It is certified that error appears in the above-identified patent and that said Letters Patent is hereby corrected as shown below:

In the Specification

At Column 1, Lines 20-25:
"The work described herein has been supported by the United States Department of Education grant number P116Z080112 and the United States National Institutes of Health-National Institutes of Aging grant number R21AG033256. As such the United States Government may have certain rights to the inventions described herein."

Should read:
-- This invention was made with government support under grant number R21 AG033256 awarded by the National Institutes of Health and support under grant number P116Z080112 awarded by the Department of Education. The government has certain rights in the invention. --

Signed and Sealed this
Third Day of December, 2019

Andrei Iancu
*Director of the United States Patent and Trademark Office*